United States Patent [19]
Teeter et al.

[11] Patent Number: 6,090,849
[45] Date of Patent: Jul. 18, 2000

[54] CARNITINE SUPPLEMENTED DIET TO PREVENT SUDDEN DEATH SYNDROME IN BREEDER TYPE POULTRY

[75] Inventors: Robert G. Teeter, Stillwater; Stanley L. Vanhooser, Glencoe, both of Okla.; Kevin Q. Owen, Manhattan, Kans.

[73] Assignees: The Board of Regents for Oklahoma State University, Stillwater, Okla.; Lonza, Inc., Fair Lawn, N.J.

[21] Appl. No.: 09/273,651

[22] Filed: Mar. 23, 1999

[51] Int. Cl.[7] ................................................. A61K 31/205
[52] U.S. Cl. .............................................................. 514/556
[58] Field of Search ............................................... 514/556

[56] References Cited

U.S. PATENT DOCUMENTS

| | | | |
|---|---|---|---|
| 4,075,352 | 2/1978 | De Felice | 424/319 |
| 4,970,080 | 11/1990 | Laurent et al. | 424/684 |
| 5,030,657 | 7/1991 | Burtle et al. | 514/556 |
| 5,124,357 | 6/1992 | Newton et al. | 514/554 |
| 5,192,804 | 3/1993 | Blum et al. | 514/554 |
| 5,213,815 | 5/1993 | O'Brien | 424/935 |
| 5,362,753 | 11/1994 | Blum et al. | 514/556 |
| 5,722,346 | 3/1998 | Tremblay et al. | 119/230 |

FOREIGN PATENT DOCUMENTS

| | | |
|---|---|---|
| WO 98/24328 | 6/1998 | WIPO . |
| WO 98/43617 | 10/1998 | WIPO . |

*Primary Examiner*—Phyllis G. Spivack
*Attorney, Agent, or Firm*—Fellers, Snider, Blankenship, Bailey & Tippens, P.C.

[57] ABSTRACT

An effective amount of carnitine is administered to broiler breeder type poultry to prevent sudden death syndrome. In the preferred embodiment, a carnitine supplemented diet is fed to broiler breeder type chickens in a feed composition during a period of time preceding peak egg production. The feed composition preferably contains between 5 and 1000 ppm of carnitine.

12 Claims, No Drawings

CARNITINE SUPPLEMENTED DIET TO PREVENT SUDDEN DEATH SYNDROME IN BREEDER TYPE POULTRY

BACKGROUND OF THE INVENTION

1. Field of Invention

The present invention relates generally to disease prevention in livestock, and, more specifically, to the prevention of sudden death syndrome in broiler breeder strain poultry.

2. Background

Sudden death syndrome (SDS), also known as Acute Death Syndrome or "Flip-Over," is characterized by high mortality (12–18%) in breeder hens during a period of high metabolic stress between the onset of lay and peak egg production without any premonitory signs. Chickens and turkeys that die of SDS are most often found lying on their backs. First recognized in Australia in the late 1970's and in Europe and U.S. flocks in the 1980's, a specific etiology for the syndrome has not been identified. The disease is known, however, to be a cardiovascular disorder and is evidenced by abnormal cardiac traits and lesions. Though mortality has been associated with the effects of an imbalance or deficit of potassium, calcium or phosphorus on metabolism during egg production, therapies directed to these areas have not proved successful.

Changing epizootiology suggests that SDS is developing into a major worldwide enzootic threat to the poultry industry. Exacerbating the stress associated with the onset of lay is the high growth rate and high metabolic demands of today's genetically engineered birds. The desire to achieve rapidly growing lean strains of meat poultry and the demands from processors to increase yields by reducing the overall size of visceral organs has meant a selection of strains susceptible to sudden death syndrome. To put it in perspective, the age to slaughter and the amount of feed required to produce a given quantity of chicken meat has been more than halved since the early 1950's. See Havenstein, G. B., P. R. Ferket, S. E. Scheldeler and B. T. Larson, *Growth, Livability and Feed Conversion of 1957 vs. 1991 Broilers When Fed "Typical" 1957 and 1991 Broiler Diets, Poultry Science*, Vol. 73, pp. 1785–1794 (1994). In the early 1950's the average length of time required to grow a broiler chicken to a 4 pound harvest weight exceeded 15 weeks. Through genetic selection, this time period has been reduced to a current average of about 6 weeks. Consequently, bird metabolic events that are needed to produce a unit of poultry meat have been squeezed into a shorter time period, creating a high metabolic demand in today's bird. Such metabolic demand is further elevated by environmental factors, such as low and high ambient temperature, and disease. As a bird having a high metabolic demand possesses a higher oxygen requirement, severe stress is placed on the bird's cardiovascular support system.

The broiler breeder experiences a demanding combination of the aforementioned stresses. While it is genetically engineered to possess a high growth rate, it must also undergo the stress of egg production.

In low total mortality flocks, a 1 to 2% incidence of SDS has a major economic impact. Thus, there exists a need to lower the incidence of sudden death syndrome among the broiler breeder subset of the poultry populace. The present inventors have surprisingly discovered that a carnitine supplemented diet for broiler breeder strain poultry fed early in the egg production cycle, such as during the stressful period just preceding the onset of lay and continuing to peak egg production, prevents the cardiac malformations associated with SDS in the targeted poultry demographic.

Heretofore, carnitine in poultry diet has been reported to have no beneficial effect on feed intake, body and abdominal fat weight or on carcass or liver lipid levels in growing broilers (Cartwright, *Poultry Science*, Vol. 65, Suppl. 1, p. 21, 1986). Dietary carnitine has been shown to retard ethanol metabolism in broilers (Smith et al., *Poultry Science*, Vol. 71, Suppl. 1, p. 64, 1992). Carnitine in poultry diet has also been shown, in U.S. Pat. No. 5,362,753, to increase the hatchability of eggs laid by breeder hens. It should be noted, however, with respect to the latter reference, that the primary efficacy of that invention relates, as shown in Table 1 of the '753 patent, to hatchability at the time of efficient egg production, i.e., at peak egg production and beyond. The '753 reference must further be noted to concern increasing the carnitine concentration in the egg such as to allow the embryo to more easily employ the stored fat of the egg. Nothing within the four corners of the '753 reference teaches or suggests any benefit to the breeder hen who has consumed the carnitine supplemented ration.

Unrelated to poultry, carnitine has been used as a supplement in pig diets (U.S. Pat. Nos. 5,124,357 and 5,192,804 and PCT Publication WO 98/24328), a smolting feed for salmon (U.S. Pat. No. 5,722,346) and in a catfish diet (U.S. Pat. No. 5,030,657). The use of carnitine in the treatment of heart failure or myocardial ischemia is discussed in U.S. Pat. No. 4,075,352 and PCT Publication WO 98/43617.

Notwithstanding the known uses of carnitine, the prior art wholly fails to teach or suggest as disclosed and claimed herein a carnitine supplemented diet fed to broiler breeder strain poultry early in the egg production cycle to prevent sudden death syndrome.

BRIEF SUMMARY OF THE INVENTION

In connection with the present invention, an effective amount of carnitine is administered to broiler breeder strain hens to prevent sudden death syndrome. Preferably, L-carnitine is administered as a supplement to the birds' food or water supply. Application in a feed composition is most preferred, wherein the amount of L-carnitine provided is between 5 to 1000 parts per million (ppm), and most preferably about 10–400 ppm, of the feed composition.

In a particularly preferred aspect of the invention the carnitine supplemented diet is fed to broiler breeder chickens early in the egg production cycle, such as between 18 and 32 weeks of age, to prevent sudden death syndrome. The inventive diet may also be useful to prevent SDS in molted birds beginning a second production cycle.

A better understanding of the present invention and its objects and advantages will become apparent to those skilled in this art from the following detailed description, wherein there is described only the preferred embodiment of the invention, simply by way of illustration of the best mode contemplated for carrying out the invention. As will be realized, the invention is capable of modifications in various obvious respects, all without departing from the scope and spirit of the invention. Accordingly, the description should be regarded as illustrative in nature and not as restrictive.

DETAILED DESCRIPTION OF THE PREFERRED EMBODIMENT

Carnitine, chemically known as 3-hydroxy-4-N-trimethylaminobutyric acid or, alternatively, β-hydroxy-γ-trimethylaminobutyric acid, is a quaternary ammonium compound present in vertebrate muscle whose metabolic function involves the transfer of fatty acids across mitochondrial membranes. Like many other biological molecules, carnitine comes in two forms: L-carnitine and D-carnitine. As used herein the term "carnitine" refers to L-carnitine and/or pharmaceutically acceptable non-toxic salts thereof, non-limiting examples of which are tartrate, fumerate and magnesium citrate.

The term "poultry" is used herein in its normal broad sense, referring to birds of several species, including chickens, turkeys, ducks, geese, swans, guineas, pigeons, peafowl, ostriches, pheasants, quail and other game birds. The term "pullet" refers to young female chickens between 10 and 32 weeks of age and denotes "egg-type" birds which produce eggs for hatching (such as broiler breeder hens). The inventors have surprisingly discovered that a carnitine supplemented diet fed to poultry, and particularly pullets, reduces the incidence of cardiomyopathy and cardiac lesions associated with the development of SDS. The theorized mode of action is the enhancement of lipid energy utilization within the heart for the generation of ATP and enhanced cardiac contractile function.

A peak energy demand period in the life of poultry occurs in broiler breeder strain female birds between the onset of lay and the time of peak egg production. In chickens, this life phase generally corresponds to between 21 and 32 weeks of age. At this time the bird is experiencing both the stress of rapid tissue accretion and the energy demands of egg production. It is at this time that female birds are most prone to develop SDS. The inventive diet when provided 2–4 weeks before the onset of lay and to the time of peak egg production positively affects cardiac traits associated with SDS.

The inventive diet is also believed to be useful in the prevention of SDS in older molted birds undergoing a second egg production cycle when fed immediately prior to and during the early stages of a second production cycle. As used herein, "onset of lay" also includes the onset of lay associated with a second production cycle. It is also believed that further supplementation, through perhaps 60 weeks of age in a bird undergoing its first production cycle, should be beneficial for poultry undergoing the stress of continued egg production.

In connection with the present invention, supplemental carnitine is provided to young broiler breeder hens during the aforementioned stress periods in an effective amount, where the desired effect is a decrease in the incidence of sudden death syndrome. This decrease can be of any level below the disease incidence of hens fed a diet without the carnitine supplement.

It is preferred that the supplemental carnitine be provided in the diet of the birds, in either solid or liquid form, and, most preferably, as part of a feed composition. The necessary concentration of carnitine for a particular species and breed of poultry being fed may be optimized by one of ordinary skill by testing a range of carnitine concentrations using trial feed compositions. With chickens, an effective amount of carnitine will range from about 5 ppm of the feed composition upwards. While no upper limit has been established as being counterproductive to the aims of the present invention (for convenience an upper range of 1000 ppm is suggested), the best known mode to practice the invention currently contemplates feeding a carnitine supplemented diet wherein the effective amount of carnitine is from about 10 ppm to about 400 ppm of the feed composition, and, most preferably, about 40 ppm of the feed composition.

The basal diet to which the carnitine is added can be any typical poultry diet meeting the nutritive needs of the bird. A conventional diet includes selections among various protein, carbohydrate, vitamin and mineral sources and will generally contain about 12–25% crude protein, 0.5–10% crude fat and 2–12% crude fiber. The primary component is generally grain and processed grain by-products which supply carbohydrates and some protein. Protein meals from soybeans, alfalfa, corn gluten, cottonseed, sunflowers and other plants are often used to supply additional protein to the diet, as are animal by-products. Poultry feed compositions are generally supplemented with various vitamins and minerals, and molasses and animal fats are added to improve palatability and to increase or balance energy levels. General reference is made to National Research Council, *Nutrient Requirements of Poultry. Nutrient Requirements of Domestic Animals*. National Academy of Science, Washington, D.C. (1994), for a discussion of poultry nutrient requirements and typical poultry rations for various species and life phases of poultry, said references being incorporated herein. Typical rations are also given below in connection with the reported examples. The feed schedule and feed rates can also be any standard schedule and rate used in the art.

As carnitine is water soluble, it alternatively may be administered through the bird's water supply. However, as water consumption varies according to the type of feed consumed, temperature, humidity, and activity of the bird, intake must be carefully monitored. The ratio of water to feed consumption in chickens generally ranges from 1.5–3.0 to 1, but may exceed 4-1 during high ambient temperature exposure or during periods of prolonged stress.

The present invention will be further understood by reference to the following non-limiting example.

EXAMPLE

Materials and Methods: Ninety Cobb X Cobb broiler breeders, twenty weeks of age were weighed and randomly assigned to individual layer cages. All birds were provided with 120 grams of feed containing 2904 kcal ME/kg, 16% protein, 0.74% lysine, and 0.32% methionine, meeting or exceeding recommended levels from the breeder (Cobb Vantress of Siloam Springs, Ark.). Water was provided for ad libitum consumption. At 24 weeks of age, controlled lighting was increased to 16 hours of light per day, feed was increased to 130 g daily, and the birds were randomly assigned to one of six dietary treatments (Table 1), which contained potassium (1.0%), antioxidants (0.1%), carnitine (200 ppm), potassium+carnitine, antioxidant+carnitine, or no supplementation (Control). Each diet contained 2.9% calcium.

TABLE 1

| | Composition of experimental diets. | | | | | |
|---|---|---|---|---|---|---|
| Ingredient | K | Anti | Carn | K and Carn | Anti and Carn | Control |
| Basal Ration[1] | 99.0 | 99.9 | 99.5 | 98.5 | 99.4 | 100 |
| $K_2HCO_3$[2] | 1.0 | — | — | — | 1.0 | — |

TABLE 1-continued

Composition of experimental diets.

| Ingredient | K | Anti | Carn | K and Carn | Anti and Carn | Control |
|---|---|---|---|---|---|---|
| Antioxidant[3] | | 0.1 | — | — | 0.1 | |
| Carnitine[4] | | | 200 ppm | 200 ppm | 200 ppm | |

[1]Calculated to contain 2904 kcal ME/kg, 16% crude protein, 0.74% lysine, 0.32% methionine, and 2.9% calcium
[2]Potassium carbonate - 65% $K^+$, Church and Dwight, Princeton, NJ 08543
[3]Antioxidant mix - Vitamin E 50% (90,700 IU/lb); Vitamin C crystal (129,572 mg/lb); Riboflavin 80 (22,675 mg/lb); Calcium carbonate 6.9%; Rice Hulls 19.5%
[4]Carnitine- L-carnitine, Lonza, Inc., Fair Lawn. NJ 07410

Individual egg production was recorded daily. Necropsies were performed on all mortalities. A sample of three birds per diet were anesthetized and subjected to a whole body scan using a Hologic x-ray bone densitometer to determine body mass composition, lean mass, percent fat and bone mass density. Blood samples were collected (2.0 mL) from these birds via venipuncture for determination of serum electrolytes.

At 31 weeks of age, blood (2.0 mL) was taken from the remaining birds via venipuncture after which they were euthanatized using $CO_2$ and necropsies were performed. Heart sections were taken and fixed in 10% buffered neutral formalin for histopathologic examination. Hearts were weighed whole and then dissected as follows. The weight of the right ventricular wall (RV), left ventricular wall (LV) and the septum (S) were recorded. Right and left ventricular wall weights were expressed relative to whole head weights and relative to body weight. A heart index was calculated as: HI=RV/LV+S. Histopathologic heart lesions were scored from one to three. The cardiac lesions of SDS have been described, and are known, in detail. A score of one indicated minimal fat deposition and myofiber size variation, whereas a score of three indicated marked foci of myocardial degeneration, arteriosclerosis and arteritis. A score of two was intermediate to the two extremes. Data were analyzed using the General Linear Models procedure of SAS (SAS Institute, 1985). Sources of variation were potassium, antioxidant, carnitine, and the interaction between potassium and carnitine. When dietary effects were present, means were separated using Duncan's Multiple Range Test (SAS Institute, 1985)

Results and Discussion: Carnitine supplementation benefitted cardiac traits (Table 2).

TABLE 2

Means of cardiac traits by diet

| Trait[3] | Diet[1] | | | | | | Source[2] | | | |
| | K | Anti | Carn | K and Carn | Anti and Carn | Control | K | Carn | K*Carn | Anti |
|---|---|---|---|---|---|---|---|---|---|---|
| HRTINDEX | 0.217[ab] | 0.198[ab] | 0.182[b] | 0.201[ab] | 0.178[b] | 0.212[a] | NS | ** | NS | NS |
| PWHLHRT | 0.0038 | 0.0037 | 0.0036 | 0.0036 | 0.0036 | 0.0037 | NS | NS | NS | NS |
| PLRVENT | 0.0022 | 0.0020 | 0.0020 | 0.0020 | 0.0021 | 0.0020 | NS | NS | NS | NS |
| PLVENT | 0.0017 | 0.0016 | 0.0017 | 0.0016 | 0.0017 | 0.0016 | NS | NS | NS | NS |
| PRTVENT | 0.0005[a] | 0.0004[ab] | 0.0004[b] | 0.0004[ab] | 0.0004[b] | 0.0004[ab] | 0 | ** | NS | NS |
| PPLVENT | 0.454[ab] | 0.430[b] | 0.461[ab] | 0.458[ab] | 0.469[a] | 0.429[b] | NS | ** | NS | NS |
| PPRTVENT | 0.127[a] | 0.106[b] | 0.103[b] | 0.115[ab] | 0.101[b] | 0.117[ab] | | ** | NS | NS |
| HSCORE | 2.44[a] | 2.73[a] | 1.93[b] | 1.87[b] | 1.87[b] | 2.53[a] | NS | ** | NS | NS |

+P ≤ 0.10,
*P ≤ 0.05,
**P ≤ 0.01,
NS = not significant.
[1]K = Basal plus potassium. Anti = Basal plus antioxidant, Carn = Basal plus carnitine, K and Carn = Basal plus potassium and carnitine, Anti and Carn = Basal plus antioxidant and carnitine, Control = Basal
[2]K = potassium supplementation, Carn = carnitine supplementation, K*Carn = the interaction between potassium and carnitine, Anti = antioxidant supplementation
[3]HRTINDEX = right ventricle wall/left ventricle wall + septum;
PWHLHRT = Whole heart weight/body weight;
PLRVENT = (left ventricle + right ventricle)/body weight;
PLVENT = left ventricle/body weight;
PRTVENT = right ventricle/body weight;
PPLVENT = left ventricle/whole heart weight,
PPRTVENT = right ventricle/whole heart weight;
HSCORE = a subjective score from 1 to 3 indicating no to severe myocardial degeneration.
[a,b]Means with no common letter superscripts differ (P ≤ 0.05).

Heart index, heart scores, and right ventricle weights (relative to body weight (BW) and relative to heart weight) were all improved by carnitine supplementation. Left ventricle weights were improved relative to heart weight. The results of this study indicate that dietary carnitine reduced undesirable cardiac traits associated with SDS. This suggests the use of carnitine in broiler breeder strain poultry during the early phase of the egg production cycle, such as just prior to the onset of lay and between the onset of lay and peak egg production in a first egg production cycle. From the experimental data and with knowledge of the field it is reasonable to extrapolate an effective range of supplementation of between 5–1000 ppm.

While the invention has been described with a certain degree of particularity, it is understood that the invention is not limited to the embodiment(s) set for herein for purposes of exemplification, but is to be limited only by the scope of the attached claim or claims, including the full range of equivalency to which each element thereof is entitled.

What is claimed is:

1. A method for preventing sudden death syndrome in broiler breeder type poultry, which comprises providing to a bird of the subject type during a period of time preceding peak egg production an effective amount of carnitine.

2. The method according to claim 1, wherein the period of time is further defined as 2–4 weeks preceding the onset of lay to the time of peak egg production.

3. The method according to claim 1, wherein the bird is a pullet.

4. The method according to claim 3, wherein the period of time is between 18 and 32 weeks of age.

5. The method according to claim 1, wherein the carnitine is L-carnitine.

6. The method according to claim 1, further comprising feeding the carnitine to the bird in a feed composition.

7. The method according to claim 6, wherein the effective amount of carnitine is from about 5 ppm to about 1000 ppm of the feed composition.

8. The method according to claim 7, wherein the effective amount of carnitine is about 10–400 ppm of the feed composition.

9. The method according to claim 8, wherein the effective amount of carnitine is about 40 ppm of the feed composition.

10. The method according to claim 1, further comprising providing the carnitine to the bird via its water supply.

11. A method for preventing or alleviating sudden death syndrome in genetically engineered poultry having a high metabolic demand, which comprises providing to a genetically engineered broiler breeder an effective amount of carnitine during a period of time preceding peak egg production.

12. The method according to claim 11, wherein the period of time is further defined as 2–4 weeks preceding the onset of lay to the time of peak egg production.

* * * * *